(12) United States Patent
Poigny et al.

(10) Patent No.: US 9,993,518 B2
(45) Date of Patent: Jun. 12, 2018

(54) ASSOCIATION OF A TETRAPEPTIDE AND A GLYCERYL ESTER FOR TREATING ANDROGENIC ALOPECIA

(71) Applicant: PIERRE FABRE DERMO-COSMETIQUE, Boulogne-Billancourt (FR)

(72) Inventors: Stéphane Poigny, Saubens (FR); Marguerite Leveque, Toulouse (FR); Laetitia Lemercier, Toulouse (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days. days.

(21) Appl. No.: 15/311,445

(22) PCT Filed: May 13, 2015

(86) PCT No.: PCT/EP2015/060644
§ 371 (c)(1),
(2) Date: Nov. 15, 2016

(87) PCT Pub. No.: WO2015/173326
PCT Pub. Date: Nov. 19, 2015

(65) Prior Publication Data
US 2017/0080046 A1 Mar. 23, 2017

(30) Foreign Application Priority Data
May 16, 2014 (FR) ...................... 14 54401

(51) Int. Cl.
| | |
|---|---|
| *A61K 38/07* | (2006.01) |
| *A61K 45/06* | (2006.01) |
| *A61K 8/64* | (2006.01) |
| *C07K 5/10* | (2006.01) |
| *A61K 8/37* | (2006.01) |
| *A61Q 7/00* | (2006.01) |
| *A61K 31/455* | (2006.01) |
| *A61K 31/661* | (2006.01) |
| *A61K 8/49* | (2006.01) |
| *A61K 8/60* | (2006.01) |
| *A61K 31/465* | (2006.01) |
| *A61K 31/7084* | (2006.01) |

(52) U.S. Cl.
CPC ............. *A61K 38/07* (2013.01); *A61K 8/375* (2013.01); *A61K 8/49* (2013.01); *A61K 8/606* (2013.01); *A61K 8/64* (2013.01); *A61K 31/455* (2013.01); *A61K 31/465* (2013.01); *A61K 31/661* (2013.01); *A61K 31/7084* (2013.01); *A61K 45/06* (2013.01); *A61Q 7/00* (2013.01); *A61K 2800/74* (2013.01)

(58) Field of Classification Search
CPC ................ A61K 31/455; A61K 31/661; A61K 2800/74; A61K 31/465; A61K 31/7084; A61K 38/07; A61K 45/06; A61K 8/375; A61K 8/49; A61K 8/606; A61K 8/64; A61Q 7/00; C07K 5/10
USPC ...... 530/300, 330; 514/20.7, 1.1, 21.9, 18.6, 514/18.8
See application file for complete search history.

(56) References Cited

U.S. PATENT DOCUMENTS

| | | | |
|---|---|---|---|
| 2006/0029563 A1* | 2/2006 | Thorel ...................... | A61K 8/60 424/70.14 |
| 2007/0004633 A1 | 1/2007 | Pinel et al. | |
| 2010/0311667 A1* | 12/2010 | Hocquaux ................ | A61K 8/64 514/18.8 |
| 2012/0195969 A1* | 8/2012 | Riordan ................. | A61K 38/18 424/529 |
| 2014/0315950 A1 | 10/2014 | Redoules et al. | |

FOREIGN PATENT DOCUMENTS

| | | |
|---|---|---|
| EP | 1338402 A1 | 8/2003 |
| FR | 2 857 597 A1 | 1/2005 |
| WO | WO 92/21320 A1 | 12/1992 |
| WO | WO 2013/083825 A1 | 6/2013 |

OTHER PUBLICATIONS

Cotsarelis, "The Hair Follicle," American Journal of Pathology, vol. 151, No. 6, Dec. 1997, pp. 1505-1509.
French Search Report for French Application No. 1454401, dated Dec. 23, 2014.
Karnik et al., "Microarray Analysis of Androgenetic and Senescent Alopecia: Comparison of Gene Expression Shows Two Distinct Profiles," Journal of Dermatological Science, vol. 72, 2013 (dated Oct. 8, 2012), pp. 183-186.
Krause et al., "Biology of the Hair Follicle: The Basics," Seminars in Cutaneous Medicine and Surgery, vol. 25, 2006, pp. 2-10.
Lachgar et al., "Vascular Endothelial Growth Factor Is an Autocrine Growth Factor for Hair Dermal Papilla Cells," J Invest Dermatol, vol. 106, No. 1, Jan. 1996, pp. 17-23.
Lien et al., "In Vivo Transcriptional Governance of Hair Follicle Stem Cells by Canonical Wnt Regulators," Nat Cell Biol, vol. 16, No. 2, Feb. 2014, pp. 179-190 (29 pages total).
Osborne et al., "Skin Penetration Enhancers Cited in the Technical Literature," Pharmaceutical Technology, XP008134247, Nov. 1997, pp. 58-66 (35 pages total).
Reddy et al., "Expression of Frizzled Genes in Developing and Postnatal Hair Follicles," J Invest. Dermatol, vol. 123, No. 2, Aug. 2004, pp. 275-282.

(Continued)

*Primary Examiner* — Julie Ha
(74) *Attorney, Agent, or Firm* — Birch, Stewart, Kolasch & Birch, LLP

(57) ABSTRACT

An association comprising a peptide is described containing the sequence A-Lys-Gly-His-Lys-NH$_2$ (SEQ ID NO: 1), wherein A is the radical corresponding to a $C_1$ to $C_{18}$ saturated or unsaturated fatty acid, and glyceryl laurate or one of the derivatives thereof. The use thereof for stimulating hair growth is also described.

19 Claims, No Drawings

(56) References Cited

OTHER PUBLICATIONS

Whiting et al., "Measuring Reversal of Hair Miniaturization in Androgenetic Alopecia by Follicular Counts in Horizontal Sections of Serial Scalp Biopsies . . . ," J of Invest Dermatol Symposium Proceedings, vol. 4, No. 3, Dec. 1999, pp. 282-284.
International Search Report issued in PCT/EP2015/060644, dated Sep. 22, 2015.
Written Opinion of the International Searching Authority issued in PCT/EP2015/060644, dated Sep. 22, 2015.

* cited by examiner

```
SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Peptide associated to glyceryl laurate
<220> FEATURE:
<221> NAME/KEY: BINDING
<222> LOCATION: (1)..(1)
<223> OTHER INFORMATION: Bond to radical A corresponding to a C1-C18
      saturated or unsaturated fatty acid and glyceryl laurate or one of
      the derivatives thereof.
<220> FEATURE:
<221> NAME/KEY: MOD_RES
<222> LOCATION: (4)..(4)
<223> OTHER INFORMATION: AMIDATION

<400> SEQUENCE: 1

Lys Gly His Lys
1
```

ASSOCIATION OF A TETRAPEPTIDE AND A GLYCERYL ESTER FOR TREATING ANDROGENIC ALOPECIA

The present invention relates to a novel association of a peptide conjugate containing the sequence Lys-Gly-His-Lys (SEQ ID NO: 1) and glyceryl laurate or a derivative thereof, and to the use of said association in the field of hair science in order to combat miniaturization of the hair and to treat androgenic alopecia.

The hair follicle is a mini-organ anchored in the skin to the hypodermis, whose principal function is the production of a hair shaft. It consists of a connective tissue sheath (CTS) formed by fibroblasts and extracellular matrix proteins, an outer root sheath (ORS) and an inner root sheath (IRS), which form a wall serving as a guide for the hair shaft as it grows. At the proximal end of the follicle is the hair bulb. It is composed of the dermal papilla, melanocytes and matrix cells, which are progenitors of follicular keratinocytes of the IRS and of the hair shaft. The dermal papilla consists of specialized fibroblasts in contact with the blood vessel system and plays an essential role in hair growth. The hair follicle also comprises a reserve of epithelial and melanocyte stem cells located under the sebaceous gland and within the outer root sheath: the bulge. These cells are characterized by a slow cell cycle and an ability to differentiate into several cell types, including matrix cells (K. Krause and K. Foitzik, Semin Cutan Med Surg, 2006; G. Cotsarelis, American Journal of Pathology, 1997).

The hair growth cycle is represented in time by three phases (anagen, catagen, telogen), the most important of which is the anagen phase (the hair shaft growth phase).

Androgenic alopecia is due to an acceleration of the hair cycle (shortening of the length of the hair cycle), a phenomenon which leads first to the appearance of miniaturized or "vellus" hair, then to premature exhaustion of the hair replacement process. Indeed, the length of the anagen (growth) phase becomes shorter and decreases from several years (2 to 5 years) to several months, even to several weeks (Whiting et al., J Investig Dermatol Symp Proc, 1999). The consequence is early hair loss.

It is known today that the mechanisms responsible for androgenic alopecia involve, intern alia, a hormonal component with overexpression of the androgen receptor (=testosterone and DHT receptor) and greater 5-alpha-reductase enzyme activity. This hormonal dysregulation leads to excessive production of dihydrotestosterone, an active metabolite of testosterone. In the dermal papilla, this metabolite stimulates the production of hair cycle inhibitors, leading to a shortening of the anagen phase and, necessarily after several cycles, an exhaustion of the hair follicle's capacity to produce a hair shaft.

A property also exploited in the general treatment of hair loss is directed at stimulating the production of VEGF, an angiogenic growth factor.

Indeed, the dermal papilla, the structure which controls hair growth, is characterized by the presence of a highly developed vascular network in the anagen phase. It has been shown that the cells of this papilla express during this stage, and in an intense fashion, the angiogenic growth factor VEGF (S. Lachgar M. Charveron in "Hair for the next millenium"-Eds. D J J Van Neste-V A Randall-H. Baden-H. Ogawa and R. Oliver-Elsevier-Amsterdam-1996-p. 407-412). This vascular endothelial growth factor maintains the vascularization necessary to the growth of new hair and its development throughout the anagen phase.

Expression of the various hair cycle regulators is modulated by various cell signaling pathways, whether to activate cell growth and differentiation during the anagen phase or to establish massive apoptosis when passing to the catagen phase. These pathways are themselves regulated by inducers and inhibitors whose levels vary as a function of the phases of the cycle, thus allowing perfectly controlled transitions from phase to phase.

Recently, certain work has suggested a major role of the Wnt/beta-catenin pathway in ensuring a normal hair cycle (Lien et al., Nature Cell Biology, 2014). This signaling pathway would indeed be heavily involved in high cell-proliferation phenomena, in particular during embryogenesis and the growth phase of the hair cycle. A deficiency of this pathway would lead to a disruption of the development of the hair follicle in the anagen phase.

The invention aims at providing novel cosmetic or dermatological compositions which would make it possible to normalize Wnt/beta-catenin signaling (the canonical Wnt pathway), which plays a major role in the regeneration of hair follicle cells, and would be used in the treatment of androgenic alopecia.

The applicant has undertaken a study carried out on samples of hair follicles plucked from alopecic subjects (androgenic alopecia). This study establishes the existence of a close relationship between hair density loss in AGA and disruption of the Wnt/beta-catenin signaling pathway. This study shows that amplification of the gene encoding an inhibitor of the Wnt/beta-catenin pathway leads to an increase in the corresponding protein in follicular samples from alopecic subjects, which appears to suggest the involvement of dysregulation of the Wnt/beta-catenin pathway in the appearance of androgenic alopecia.

The applicant has shown the existence of a synergy between a peptide containing the sequence Lys-Gly-His-Lys (SEQ ID NO: 1) and glyceryl laurate or a derivative thereof to inhibit the expression level of the SFRP1 gene encoding a Wnt/beta-catenin pathway inhibitor and to stimulate the expression level of the FZD1 gene encoding a Wnt ligand receptor responsible for the activation of the Wnt/beta-catenin pathway in dermal papilla cells and matrix cells (Reddy et al., J Invest Dermatol., 2004).

In addition, there has also been shown a synergistic action of this association of active agents to activate the gene expression level of specific keratins (including KRT17, KRT25, KRT27 and KRT81) whose expression is regulated by the Wnt/beta-catenin pathway, these keratins being markers of the differentiation of epithelial stem cells of the bulb into follicular keratinocytes.

More specifically, this association of active agents will normalize the renewal of the hair cycle by restoring the Wnt/beta-catenin pathway function.

Therefore, this association of active agents will make it possible to combat hair cycle shortening (to act as a true hair growth "extender") and miniaturization of the hair.

Thus, the present invention has as an object an association comprising a peptide containing the sequence A-Lys-Gly-His-Lys-NH$_2$ (SEQ ID NO: 1) wherein A represents the radical corresponding to a $C_1$-$C_{18}$ saturated or unsaturated fatty acid, and glyceryl laurate or a derivative thereof.

In the peptide containing the sequence A-Lys-Gly-His-Lys-NH$_2$ (SEQ ID NO: 1), "A" preferentially represents the acetyl, palmityl or stearyl radical.

Such a peptide is described for example in the document EP 1 663 285.

In a particular embodiment, the peptide conjugate is acetyl tetrapeptide-3, whose sequence is: A-Lys-Gly-His- Lys-NH$_2$ (SEQ ID NO: 1), wherein A is an acetyl group; the corresponding CAS number being 827306-88-7.

The tetrapeptide will stimulate scalp microcirculation and will facilitate the supply of elements necessary to cellular metabolism.

The synergy was observed with glyceryl laurate as 5-alpha-reductase inhibitor, but this effect extends to glyceryl laurate derivatives/precursors of the following formula I

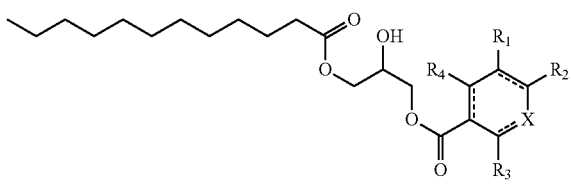

wherein
if X=NH, then each of R$_1$, R$_2$, R$_3$, R$_4$ represents a hydrogen atom;
if X=N, then the ring is aromatic and R$_1$, R$_2$, R$_3$ and R$_4$ represent hydrogen atoms, or one of which a methyl group; and when R$_2$=R$_3$=R$_4$=H, R$_1$ may also represent a halogen atom or an aryl, heteroaryl, alkenyl, acetylenyl radical.

These derivatives are described for example in the application WO2013/083825.

According to a particular embodiment of the invention, the mass ratio between the glyceryl laurate and the peptide is between 0.5 and 300, preferably between 1 and 200 and more preferentially about 100.

The present invention further relates to an association comprising a peptide containing the sequence A-Lys-Gly-His-Lys-NH$_2$ (SEQ ID NO: 1) wherein A represents the radical corresponding to a C$_1$-C$_{18}$ saturated or unsaturated fatty acid, and glyceryl laurate or a derivative thereof for topical use to treat androgenic alopecia, and to the use of the association to promote hair growth.

The present invention also relates to a cosmetic or dermatological composition comprising, as an anti-hair-loss active agent, an association comprising a peptide containing the sequence A-Lys-Gly-His-Lys (SEQ ID NO: 1) wherein A represents the radical corresponding to a C$_1$-C$_{18}$ saturated or unsaturated fatty acid, and glyceryl laurate or a derivative thereof, and further comprising at least one cosmetically or dermatologically acceptable excipient.

Preferably, the acceptable excipients are suited to topical administration.

In particular, the acceptable excipients provide good stability and a pleasant texture and feel. They may also be, for example, formulating agents or additives of known and conventional use in cosmetics: mention may be made of surfactants, colorants, preservatives, fragrances, film-forming agents, etc.

The compositions according to the invention may appear in the forms which are commonly known for topical administration on the hair and the scalp, i.e. in particular a shampoo, a conditioner, a hair cream, a hair lotion or a no-rinse spray.

In a preferred embodiment, the composition will be in the form of a no-rinse spray.

The object of the present invention is directed at the cosmetic use of the association according to the present invention or this cosmetic composition according to the invention to promote hair growth. The cosmetic use of the association according to the present invention or the cosmetic composition according to the invention is more particularly intended to regulate the hair cycle and to promote follicular regeneration.

The present invention also relates to a cosmetic hair care method for improving the aesthetics of the hair by promoting hair growth, characterized in that it consists in applying to the hair and the scalp an effective amount of an association according to the invention or a cosmetic composition according to the invention, leaving same in contact with the hair, and optionally rinsing the hair.

Another object of the present invention relates to a dermatological composition for use in the treatment of androgenic alopecia, comprising as active agent the association according to the invention.

In a preferred embodiment of the invention, the composition is intended for topical application.

In a particular embodiment, the dermatological and cosmetic compositions according to the invention comprise at least one other active agent.

This other active agent may in particular be selected from the group comprising other 5-alpha-reductase inhibitors.

According to a particular embodiment, the compositions according to the invention further comprise a nicotine derivative among which is vitamin PP (nicotinamide) or an ester selected from ethyl, methyl, 2-ethylhexyl, myristyl and benzyl nicotinates as well as alpha-tocopherol nicotinate or delta-tocopherol nicotinate.

Preferably, this additional anti-hair-loss active agent is alpha-tocopherol nicotinate. It acts as a penetration enhancer for the other active agents, it stimulates cellular metabolism and it promotes skin microcirculation (stimulation of VEGF production).

In this embodiment, the composition according to the invention comprises an association comprising a peptide containing the sequence A-Lys-Gly-His-Lys (SEQ ID NO: 1) wherein A represents the radical corresponding to a C$_1$-C$_{18}$ saturated or unsaturated fatty acid, glyceryl laurate or a derivative thereof and alpha-tocopherol nicotinate.

According to another embodiment of the invention, the composition will further comprise diguanosine tetraphosphate (GP4G).

GP4G is a marine biotechnology active agent extracted from the zooplankton *Artemia salina*, and has the following chemical structure:

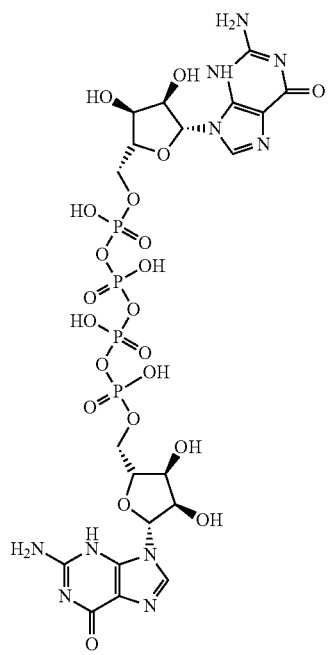

The composition according to the invention then comprises an association comprising a peptide containing the sequence A-Lys-Gly-His-Lys (SEQ ID NO: 1); glyceryl laurate or a derivative thereof and GP4G.

In a preferred embodiment, the association will further comprise tocopherol nicotinate and GP4G, with these two additional active agents acting as a vasculotropic complex (see EP1336402).

In a preferred embodiment, the tocopherol nicotinate and GP4G complex is present in the following amounts
between 0.05% and 5% by weight of tocopherol nicotinate, preferably from 0.1% to 2.5%
between 0.01% and 5% by weight of GP4G, preferably from 0.05% to 2.5% relative to the total weight of the composition.

In a preferred embodiment, the final composition will be transparent and preferably in the form of transparent lotion.

The expression "transparent composition" means a homogeneous (only one phase) and clear composition which allows light to pass, for example so as to allow the back of a label affixed to a transparent glass or plastic bottle containing said composition to be read through said bottle.

To that end, it has been shown that the solvent to be used in addition to ethanol (10% to 40%), which acts to facilitate the penetration of anti-hair-loss products, is isopropyl alcohol in an amount between 1% and 5%, and preferably 2.5% by weight relative to the total weight of the composition. It was observed that isopropyl alcohol (2.5%) plays, with active material four times less than the hexylene glycol (10%) conventionally used to improve penetration into the hair follicle, the role of solubilizing the lipophilic waxy active agents, namely tocopheryl nicotinate and glyceryl laurate, a solvent action essential for the visual quality of the product but also for increasing the bioavailability of these two active agents acting on increased blood flow and regulation of 5-alpha-reductase activity, respectively.

The light texture of said composition further allows optimal penetration without making the hair greasy. From the first applications, the hair regains strength and vitality.

The composition according to the invention makes it possible to stop hair loss and to extend the hair cycle. Existing hair is preserved in quantity and in quality.

The following examples are intended to illustrate certain particular embodiments of the invention and represent in particular certain compositions usable for implementing the invention. The excipients mentioned in the exemplary compositions are given for illustrative purposes only, and it is within the capability of persons skilled in the art to substitute others.

MATERIALS AND METHODS

Hair follicle bulbs derived from plastic surgery waste (face lifts) from two donors were isolated by microdissection, cultured and treated for 6 hours with the active agents (acetyl tetrapeptide-3, glyceryl laurate, and the association thereof). RNA was extracted, assayed, reverse-transcribed and the expression of a panel of genes expressed in the pilosebaceous follicle was analyzed by quantitative real-time PCR.

The analysis of the results generated in this study led, for each condition applied and each gene of interest studied, to the calculation of a relative quantity (RQ). RQ corresponds to the expression level of a gene relative to its basal expression level (expression level obtained for the Control condition, the RQ of which is set to 1). Thus, the modulation of a gene's expression level is considered significant when:
the RQ is greater than or equal to 2: the gene is expressed two times more than in the Control condition
the RQ is less than or equal to 0.5: the gene is expressed two times less than in the Control condition.

Since RQs cannot be added, an effect is regarded as synergistic when the RQ obtained with the association of active agents is significantly higher or lower than the RQs obtained for each active agent tested alone.

The set of results presented below corresponds to the average results obtained for the two donors of the study.

Results

Among the set of genes studied, 11 genes of interest are favorably regulated by the association of acetyl tetrapeptide-3 (ATP-3) and glyceryl laurate (GL), in a synergistic manner.

The association of acetyl tetrapeptide-3 and glyceryl laurate stimulates the expression level of the COL3A1 and COL7A1 genes (involved in hair follicle anchoring), and the expression of the IGF1R gene (involved in the development of the hair follicle in the anagen phase). It also appears to induce the expression of the SHH gene and to inhibit the expression of the BMP4 gene, both involved in Sonic Hedgehog signaling, which contributes to the self-renewal, proliferation and differentiation of hair follicle stem cells.

Synergistic modulation of the expression level of genes involved in the Wnt/beta-catenin signaling pathway by the association of acetyl tetrapeptide-3 and glyceryl laurate.

This signaling pathway is described to be heavily involved in the regulation of the hair cycle (telogen→anagen transition) and to play an essential role in maintaining hair follicles in the anagen phase and in producing a new hair shaft. Indeed, it stimulates the proliferation and differentiation of bulge epithelial stem cells and of progenitor cells into follicular keratinocytes. The Wnt/beta-catenin pathway is described to be inhibited by the action of androgens, the source of the advantage represented by restoring this signal in the treatment of androgenic alopecia.

The receptor "frizzled family receptor 1" (encoded by the FZD1 gene) is a transmembrane receptor of the canonical (Wnt/beta-catenin) and non-canonical Wnt pathways. In the hair follicle, it is expressed by ORS cells, matrix cells and dermal papilla cells. Its expression level, low in the telogen phase, increases at the beginning of the anagen phase (anagen onset). In the ORS, the Wnt ligands expressed most are the ligands Wnt5a and Wnt11, described to activate the non-canonical Wnt pathway, which may make it possible to regulate progenitor stem cell migration from the bulge toward the matrix. In the matrix and the dermal papilla, the Wnt ligands expressed most are the ligands Wnt10a and Wnt10b, described to activate the Wnt/beta-catenin pathway.

After 6 hours of treatment, the association of acetyl tetrapeptide-3 (ATP-3) and glyceryl laurate (GL) synergistically stimulates the expression level of the FZD1 gene.

The monitoring of the expression level of the FZD1 gene in human hair follicles is presented in Table I below:

TABLE I

| | 6 h | | | |
|---|---|---|---|---|
| | Control | ATP-3 | GL | ATP-3 + GL |
| | — | 20 µM | 10 µM | 20 µM + 10 µM |
| RQ | 1.0 | 1.2 | 1.3 | 4.4 |

The protein "secreted frizzled-related protein 1" (encoded by the SFRP1 gene) is an inhibitor of the Wnt/beta-catenin pathway. It has a domain homologous to the Wnt binding site on frizzled receptors; it is thus able to bind to Wnt proteins and to prevent them from binding to frizzled receptors, but is also able to form an inhibitor complex with frizzled receptors and thus to prevent the activation of Wnt signaling.

The article by Karnik et al. (Microarray analysis of androgenetic and senescent alopecia: Comparison of gene expression shows two distinct profiles, Journal of Dermatological Science 72 (2013) 183-183) describes various specific markers of androgenic alopecia (AGA), among which is the gene encoding the SFRP1 inhibitor which is found overexpressed by a factor of 3.73 in AGA patients compared with the control group.

After 6 hours of treatment, the association of acetyl tetrapeptide-3 (ATP-3) and glyceryl laurate (GL) synergistically inhibits the expression level of the SFRP1 gene.

The monitoring of the expression level of the SFRP1 gene in human hair follicles is presented in Table II below:

TABLE II

|    | 6 h     |                |              |                         |
|----|---------|----------------|--------------|-------------------------|
|    | Control | ATP-3<br>20 μM | GL<br>10 μM  | ATP-3 + GL<br>20 μM + 10 μM |
| RQ | 1.0     | 1.3            | 0.9          | 0.4                     |

During the telogen-anagen transition and at the beginning of the anagen phase, bulge epithelial stem cells differentiate into follicular keratinocytes in order to generate the concentric layers forming the ORS, the IRS and the hair shaft necessary to the regeneration of the hair follicle. Each layer making up the follicle is characterized by a type of keratinocyte producing a panel of proteins, mainly keratins, which is distinctive to it. Keratins are thus markers of this differentiation and their expression is, for the most part, regulated by the Wnt/beta-catenin signaling pathway.

Keratin 17, encoded by the KRT17 gene, is expressed by follicular keratinocytes of the ORS. Keratins 25 and 27, encoded by the KRT25 and KRT27 genes, respectively, are expressed by follicular keratinocytes of the IRS. Keratin 81, encoded by the KRT81 gene, is expressed by follicular keratinocytes of the cortex.

The article by Karnik et al. (Microarray analysis of androgenetic and senescent alopecia: Comparison of gene expression shows two distinct profiles, Journal of Dermatological Science 72 (2013) 183-183) also showed keratin 27 as being a specific marker of AGA, the KRT27 gene being found underexpressed by a factor of 4.92 in AGA patients compared with the control group.

After 6 hours of treatment, the association of acetyl tetrapeptide-3 (ATP-3) and glyceryl laurate (GL) synergistically stimulates the gene expression level of keratins 17, 25, 27 and 81.

The monitoring of the expression level of the KRT17 gene in human hair follicles is presented in Table III below:

TABLE III

|    | 6 h     |                |              |                         |
|----|---------|----------------|--------------|-------------------------|
|    | Control | ATP-3<br>20 μM | GL<br>10 μM  | ATP-3 + GL<br>20 μM + 10 μM |
| RQ | 1.0     | 0.8            | 1.1          | 2.3                     |

The monitoring of the expression level of the KRT25 gene in human hair follicles is presented in Table IV below:

TABLE IV

|    | 6 h     |                |              |                         |
|----|---------|----------------|--------------|-------------------------|
|    | Control | ATP-3<br>20 μM | GL<br>10 μM  | ATP-3 + GL<br>20 μM + 10 μM |
| RQ | 1.0     | 1.7            | 1.3          | 6.8                     |

The monitoring of the expression level of the KRT27 gene in human hair follicles is presented in Table V below:

TABLE V

|    | 6 h     |                |              |                         |
|----|---------|----------------|--------------|-------------------------|
|    | Control | ATP-3<br>20 μM | GL<br>10 μM  | ATP-3 + GL<br>20 μM + 10 μM |
| RQ | 1.0     | 1.4            | 1.3          | 3.2                     |

The monitoring of the expression level of the KRT81 gene in human hair follicles is presented in Table VI below:

TABLE VI

|    | 6 h     |                |              |                         |
|----|---------|----------------|--------------|-------------------------|
|    | Control | ATP-3<br>20 μM | GL<br>10 μM  | ATP-3 + GL<br>20 μM + 10 μM |
| RQ | 1.0     | 1.5            | 1.8          | 4.0                     |

Two examples of transparent lotions are given below by way of simple illustration of the object of the invention:

Example 1: Transparent Lotion

ACETYL TETRAPEPTIDE-3 PP from 0.001 to 0.01%
GLYCERYL LAURATE from 0.05 to 0.3%
GP4G from 0.01 to 5%
TOCOPHERYL NICOTINATE 0.05 to 5%
DEXPANTHENOL from 0.3 to 1%
ISOPROPYL ALCOHOL from 1 to 5%
PPG-26-BUT.-26/PEG-40 from 2 to 10%
ETHYL ALCOHOL from 10 to 40%
FRAGRANCE q.s.
WATER q.s.

Example 2: Transparent Lotion

ACETYL TETRAPEPTIDE-3 PP from 0.001 to 0.01%
GLYCERYL LAURATE from 0.05 to 0.3%
GP4G from 0.01 to 5%
TOCOPHERYL NICOTINATE 0.05 to 5%
DEXPANTHENOL from 0.3 to 1%
BETAINE HYDRATE from 0.5 to 3%
ISOPROPYL ALCOHOL from 1 to 5%
PPG-26-BUT.-26/PEG-40 from 2 to 10%
ETHYL ALCOHOL from 10 to 40%
FRAGRANCE q.s.
WATER q.s.

The invention claimed is:

1. An association comprising:
   a peptide containing the sequence A-Lys-Gly-His-Lys-NH$_2$ (SEQ ID NO: 1), wherein A represents acetyl, palmityl or stearyl radical;
   glyceryl laurate or a derivative thereof.

2. The association according to claim 1, wherein the mass ratio between the glyceryl laurate and the peptide is between 0.5 and 300.

3. The association according to claim 1, for topical use to treat androgenic alopecia.

4. The association according to claim 1, wherein the derivative thereof is represented by the following formula I:

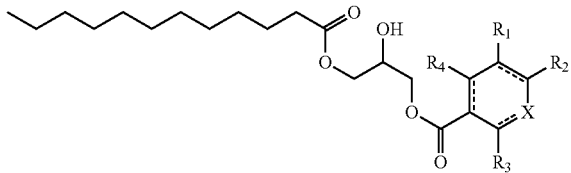

wherein
   if X=NH, then each of R$_1$, R$_2$, R$_3$, R$_4$ represents a hydrogen atom;
   if X=N, then the ring is aromatic and R$_1$, R$_2$, R$_3$ and R$_4$ represent hydrogen atoms, or one of which a methyl group; and when R$_2$=R$_3$=R$_4$=H, R$_1$ may also represent a halogen atom or an aryl, heteroaryl, alkenyl, acetylenyl radical.

5. The association according to claim 2, for topical use to treat androgenic alopecia.

6. The association according to claim 2, wherein the mass ratio between the glyceryl laurate and the peptide is between 1 and 200.

7. The association according to claim 2, wherein the mass ratio between the glyceryl laurate and the peptide is about 100.

8. A dermatological or a cosmetic composition comprising as active agent an association according to claim 1, with at least one dermatologically or cosmetically acceptable excipient.

9. The composition according to claim 8, wherein the peptide or peptide conjugate is present in an amount of 0.001% to 0.01% by weight of the total composition.

10. The composition according to claim 8, wherein the glyceryl laurate or derivative thereof is present in an amount of 0.05% to 0.3% by weight of the total composition.

11. The composition according to claim 8, wherein one of the excipients is isopropyl alcohol as solvent present in an amount ranging between 1% and 5%, by weight relative to the total weight of the composition.

12. The composition according to claim 8, wherein it further comprises one other active agent.

13. The composition according to claim 12, wherein the other active agent is tocopherol nicotinate.

14. The dermatological composition according to claim 8, for use in the treatment of alopecia.

15. The composition according to claim 11, wherein one of the excipients is isopropyl alcohol as solvent present in an amount of 2.5% by weight relative to the total weight of the composition.

16. The composition according to claim 12, wherein the other active agent is selected from other 5-alpha-reductase inhibitors and mixtures thereof.

17. The composition according to claim 12, wherein the other active agent is diguanosine tetraphosphate.

18. The composition according to claim 17, wherein the diguanosine tetraphosphate is present in an amount of 0.01% to 5% by weight of the total composition.

19. The composition according to claim 18, wherein the diguanosine tetraphosphate is present in an amount of 0.05% to 2.5% by weight of the total composition.

* * * * *